Aug. 15, 1972 W. H. JESSEL, JR., ETAL Plant Pat. 3,257
CHRYSANTHEMUM PLANT
Filed Jan. 29, 1971
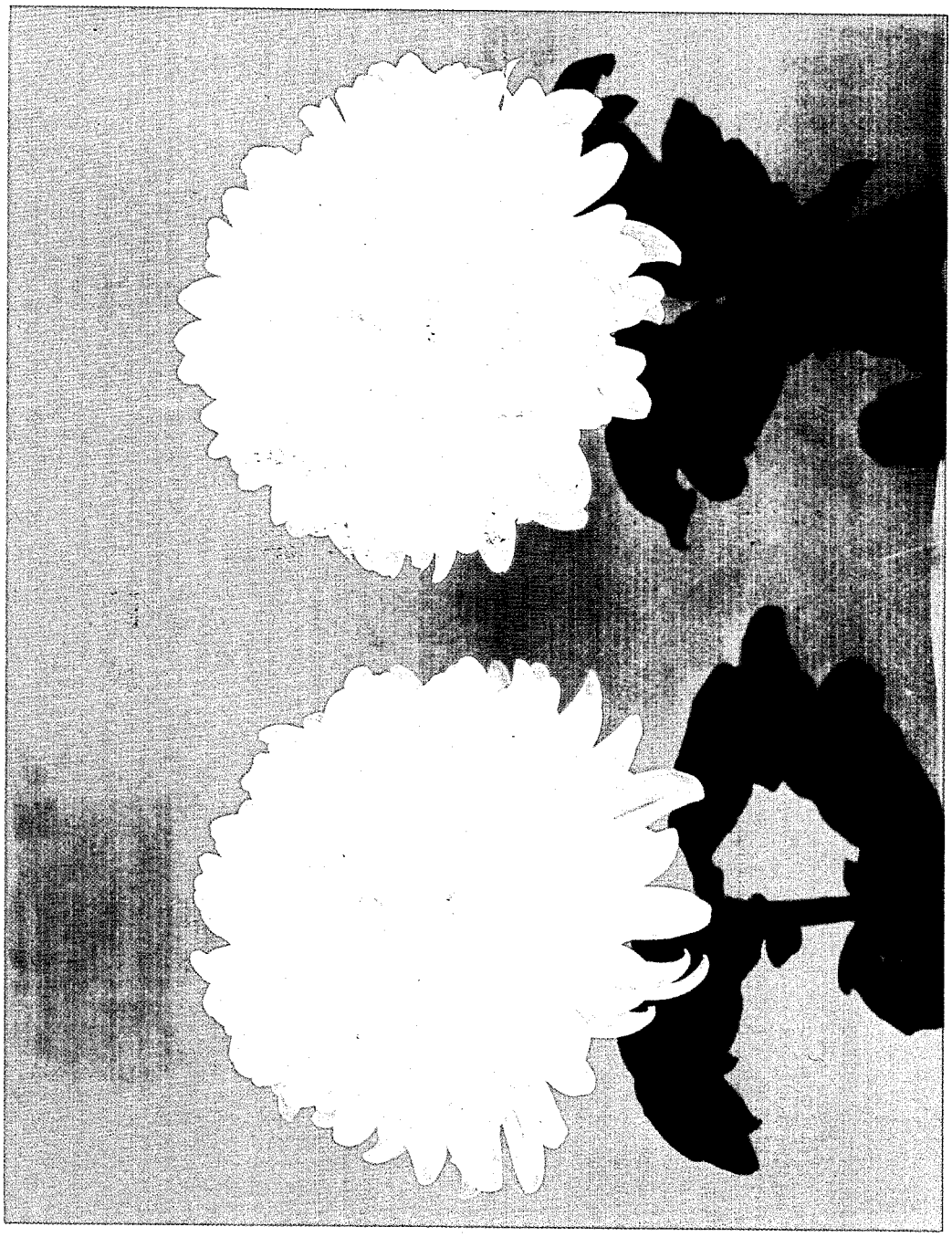
INVENTORS
WALTER H. JESSEL, JR.,
WILLIAM E. DUFFETT
BY
Oberlin, Maky, Donnelly & Renner
ATTORNEYS

United States Patent Office

Plant Pat. 3,257
Patented Aug. 15, 1972

3,257
CHRYSANTHEMUM PLANT

Walter H. Jessel, Jr., Doylestown, and William E. Duffett, Akron, Ohio, assignors to Yoder Brothers, Inc., Barberton, Ohio

Filed Jan. 29, 1971, Ser. No. 111,160
Int. Cl. A01h *5/00*
U.S. Cl. Plt.—78 1 Claim

The present invention comprises a new and distinct variety of chrysanthemum plant which is a form and color mutation of the unpatented commercial variety Southern Sun.

The new variety is similar in many respects to Southern Sun, having the same characteristics of:

(1) Leaf shape, size, color.
(2) Mid 8 to early 9 week response.
(3) Same vigorous growth habit.

The new variety is distinguished from Southern Sun by the following characteristics:

(1) More intense yellow color which is more resistant to fading.
(2) More tightly incurved flower form and improved form retention which holds from 3 to 4 days longer.
(3) Center petals swirled when opening.
(4) ½"–¾" larger flower with more uniform grade within a flowering plot.

The new variety was discovered upon examination of a flowering plot of the parent variety in a greenhouse in Barberton, Ohio. When asexually reproduced by cuttings at Barberton, Ohio, the new cultivar has been found to retain its distinctive characteristics through successive propagations.

The new variety when grown in the vicinity of Barberton, Ohio, has a response period of approximately 9 weeks, and the following detailed description is based on observations made of the new variety in a greenhouse in Barberton, Ohio. The response time and blooming period may vary significantly with varying environmental conditions such as temperature, light intensity and daylength. Suggested flowering in the northern and western United States is from May through October, and for the southern United States, from April through mid-November.

The accompanying drawing is a comparison photograph of the new cultivar and the parent cultivar Southern Sun, with the latter appearing on the right and the new cultivar on the left. It should be noted that although color differences do exist between the new and parent cultivars, as indicated by the color designations listed below, these differences are not readily apparent from the accompanying photograph.

The following is a detailed description of the new cultivar, with color references being to the Munsell Color Book, 1963 edition, and comparisons made with the parent cultivar Southern Sun. Where only a single value or description is listed for the new cultivar, such value or description applies also to the comparison cultivar.

BOTANICAL CLASSIFICATION: *Cyrsyanthemun morifolium*

| | Southern Gold | Southern Sun |
|---|---|---|
| Bloom: | | |
| Size | 5½"–6" | 5"–5½". |
| Fully expanded | 6"–7" | 5½"–6½". |
| Borne | Single on a disbudded plant. | Single on a disbudded plant. |
| Stems | Wiry | Wiry. |
| Form | Semi-incurved | Semi-incurved. |
| Permanence | 8–12 days | 8–12 days. |
| Color: | | |
| Center of flower. | Golden yellow 7.5Y8.5/10. | Light yellow 7.5Y8.50/6. |
| Base of petals | do | Do. |
| Inside of petals | do | Do. |
| Reverse of petals. | Golden yellow 7.5Y8.50/6. | Light yellow 7.5Y9/4. |
| Tonality from a distance. | Golden yellow | Lemon yellow. |
| Discoloration | Golden yellow 7.5Y8.5/10. | Yellow 7.5Y8.50/6. |

Petals:
- *Texture.*—Smooth.
- *Appearance and form.*—Sharply keeled at base, rather narrow with a blunt point.
- *Arrangement.*—Composite, whorled on a single receptacle.
- *Persistence.*—Resist shatter.
- *Fragrance.*—Typical chrysanthemum.

Reproductive organs:
- *Stamens, anthers.*—None.
- *Pollen.*—None.
- *Arrangement.*—Clustered in center of flower, if present.
- *Styles.*—Present in both ray and disc florets.
- *Length.*—Short.
- *Ovaries.*—At base of petals attached to receptacle.

Plant:
- *Form.*—Herbaceous.
- *Growth.*—Upright.
- *Height.*—46"–54" depending on culture.
- *Spread.*—None when grown single stem, to slight if pinched.

Foliage:
- *Top side.*—Dark green, 7.5GY2/4.
- *Size.*—5½" long, 3½" wide.
- *Quantity.*—Numerous.
- *Shape.*—Palmate.
- *Texture.*—Coarse.
- *Ribs and veins.*—Prominent.
- *Edge.*—Indented.
- *Serration.*—Moderate.
- *Underside.*—Light green, 7.5GY4/4.
- *Stipules.*—Present.

We claim.

1. A new and distinct variety of chrysanthemum characterized particularly as to novelty when compared to the present cultivar Southern Sun by its more intense golden yellow color and greater resistance to fading, its flowers which are ½" to ¾" larger, and its improved flower form which holds 3 to 4 days longer than the parent.

No references cited.

ROBERT E. BAGWILL, Primary Examiner